United States Patent [19]

Kurz

[11] 4,386,908
[45] Jun. 7, 1983

[54] LINGUAL ORTHODONTIC APPLIANCE SYSTEM FOR THE MANDIBULAR ARCH

[76] Inventor: Craven H. Kurz, No. 6, N. Star, Apt. 106, Marina del Rey, Calif. 90291

[21] Appl. No.: 301,452

[22] Filed: Sep. 14, 1981

Related U.S. Application Data

[63] Continuation-in-part of Ser. No. 741,850, Nov. 15, 1976, abandoned.

[51] Int. Cl.³ .............................................. A61C 3/00
[52] U.S. Cl. ............................................ 433/9; 433/8
[58] Field of Search ...................... 433/8, 9, 10, 11, 15, 433/16, 17, 18, 24

[56] References Cited

U.S. PATENT DOCUMENTS

| | | | |
|---|---|---|---|
| 3,599,331 | 8/1971 | Lee | 433/18 |
| 3,815,238 | 6/1974 | Wallshein | 433/17 |
| 3,824,503 | 10/1974 | Wildman | 433/24 |
| 3,922,787 | 12/1975 | Fischer et al. | 433/15 |
| 4,209,906 | 7/1980 | Fujita | 433/11 |
| 4,216,583 | 8/1980 | Reynolds | 433/17 |
| 4,256,455 | 3/1981 | Forster | 433/9 |

OTHER PUBLICATIONS

"Triple Action Deep Slot System", American Orthodontics Bulletin 1-79-3, 1979.

Primary Examiner—John J. Wilson
Attorney, Agent, or Firm—Keith D. Beecher

[57] ABSTRACT

A direct-bonded fixed lingual orthodontic appliance system for the mandibular arch is provided which comprises a plurality of metal or plastic attachments which are designed to be cemented directly to the lingual surfaces of the mandibular teeth, and an arch wire intercoupling the attachments extending aroumd the lingual side of the teeth. The surface of the base of each of the attachments contacting the corresponding tooth is particularly configured so as to have intimate contact with the tooth. The attachments are shaped to minimize trauma, and to provide for an arch wire configuration which does not require in-and-out bends, as the arch wire is inserted into the attachments. The attachments are also constructed to incorporate built-in angulation corrective properties for the corresponding teeth.

8 Claims, 13 Drawing Figures

BASE OF BRACKET FOR CENTRAL INCISORS

BASE OF BRACKET FOR CENTRAL INCISORS

BASE OF BRACKET FOR LATERAL INCISORS

BASE OF BRACKET FOR CUSPIDS ably affixed to the lingual surfaces of the teeth forming the illustrated mandibular arch.

LINGUAL ORTHODONTIC APPLIANCE SYSTEM FOR THE MANDIBULAR ARCH

This application is a continuation-in-part of copending application Ser. No. 741,850 which was filed Nov. 15, 1976, and now abandoned.

BACKGROUND OF THE INVENTION

The prior art arch wire fixed orthodontic appliance systems usually comprise a plurality of brackets and tubes which are cemented or banded to the labial and buccal surfaces of the respective teeth around the arch, and which are intercoupled by an arch wire extending around the external surface of the teeth. Although the prior art appliance systems are effective, they are unsightly and embarrassing to the wearer. Moreover, there is a problem in the prior art labial and buccal appliance systems of the maxillary teeth contacting and biting off the attachments, when the attachments are bonded to the respective teeth.

The direct bonded orthodontic arch wire appliance system of the present invention includes attachments which are configured to be cemented to the lingual surfaces of the mandibular teeth. The system of the invention is virtually invisible, and there is no tendency for the maxillary teeth to contact or bite off the attachments. Moreover, the system obviates any scarring of the facial enamel surfaces of the teeth.

BRIEF DESCRIPTION OF THE DRAWINGS

FIG. 7A is a sectional view of the base of FIG. 7 taken along the line 7A—7A of FIG. 7;

FIG. 8A is a section of the base taken along the line 8A—8A of FIG. 8:

FIG. 9A is a section of the base of FIG. 9 taken along the line 9A—9A of FIG. 9; and FIG. 9B is a section of the base of FIG. 9 taken along the line 9B—9B of FIG. 9;

DETAILED DESCRIPTION OF THE ILLUSTRATED EMBODIMENT

Figure 1:
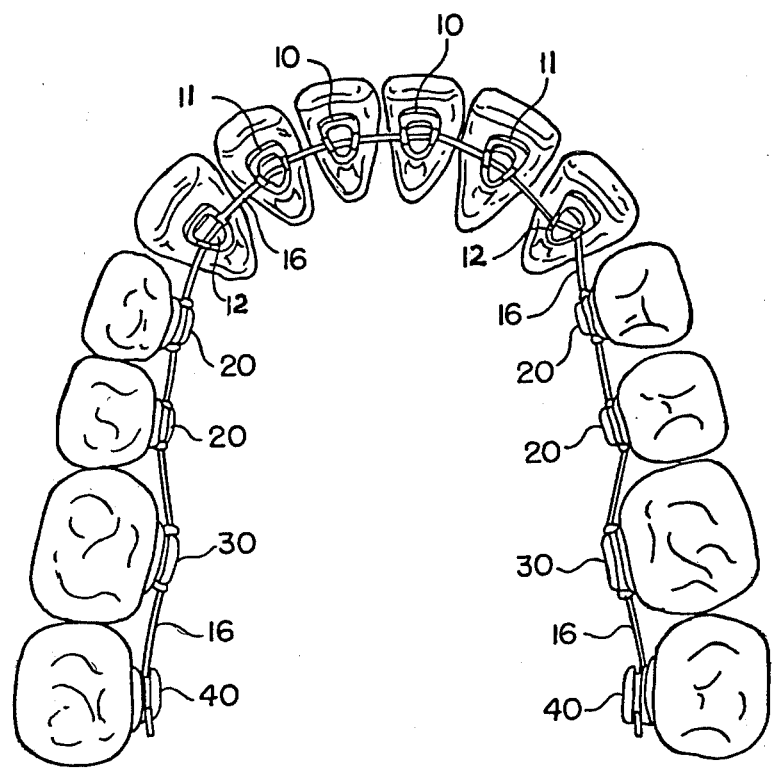
FIG. 1 is a plan view of the mandibular arch of a patient, and showing a direct bonded fixed lingual orthodontic arch wire appliance system, representative of one embodiment of the invention, in place on the lingual surfaces of the teeth forming the arch.

The bases of the attachments of the lingual appliance system of the invention are constructed to incorporate a straight wire concept, as shown in FIG. 1, by providing an individualized thickness for the attachments so that a straight contoured arch wire 16 will not require in-and-out bends, as it is inserted into the attachments. The attachments also incorporate a special built-in angulation mesio-distally, and a built-in angulation bucco-lingually and labio-lingually for that purpose.

Figure 2:
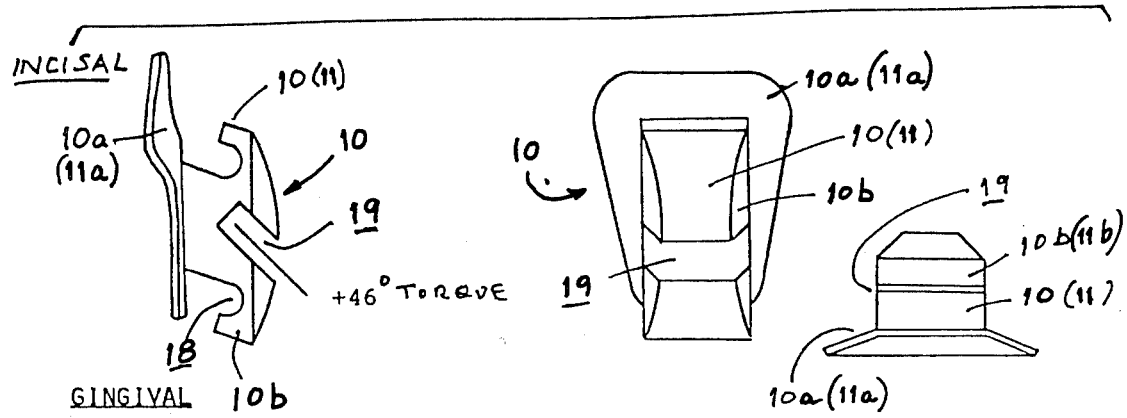
FIG. 2 represents three views of a lingual bracket suitable for use with the central and lateral incisors in the arch of FIG. 1.

In the representation of FIG. 1, a direct bonded fixed lingual arch wire appliance system, constructed in accordance with one embodiment of the invention, is shown with its attachments adhesi The orthodontic appliance system of FIG. 1 includes a plurality of brackets 10, shown in detail in FIG. 2. These brackets are adhesively attached to the lingual surfaces of the central incisors. The system of FIG. 1 also includes brackets 11, which are cemented to the lingual surfaces of the lateral incisors, and which are also shown in detail in FIG. 2. Also included in the system are brackets 12 which are cemented to the lingual surfaces of the cuspids (canines), and which are shown in more detail in FIG. 4.

Figure 4:
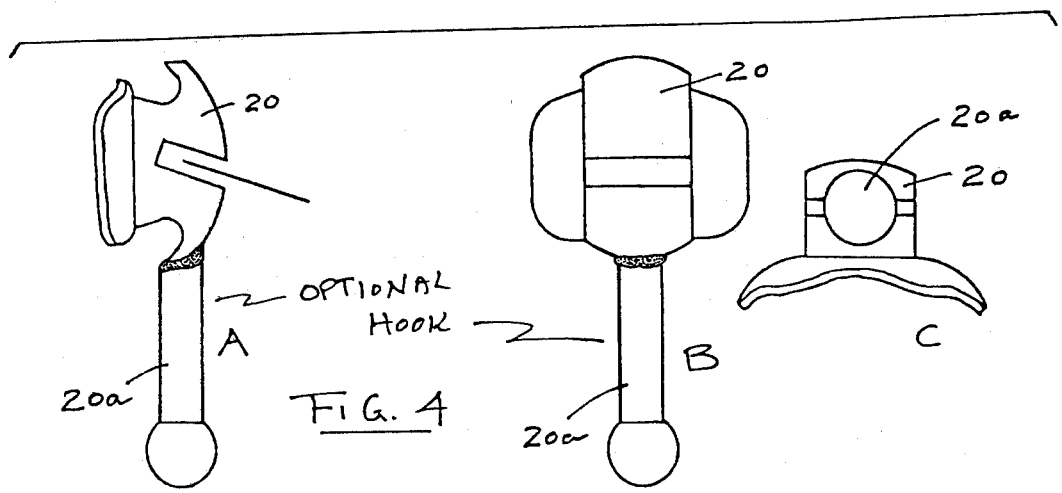
FIG. 4 represents four views of a lingual bracket suitable for use in conjunction with the bicuspids of the arch of FIG. 1.
Figure 5:
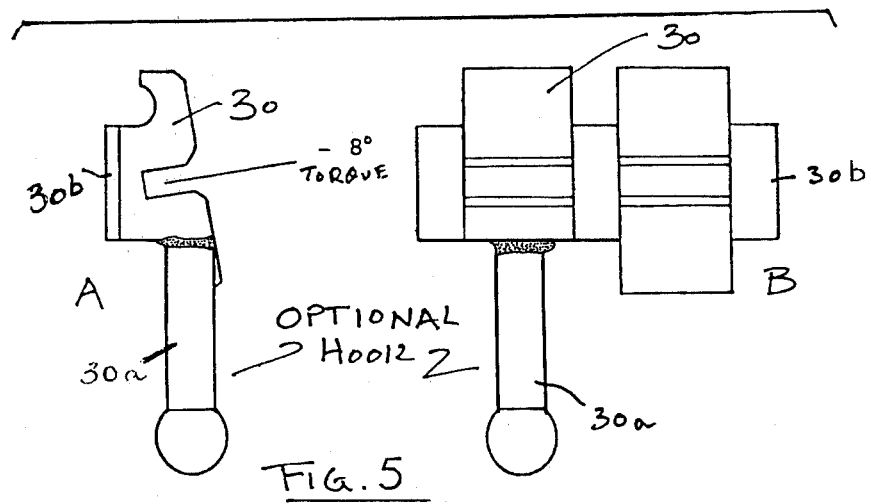
FIG. 5 represents two views of a bracket suitable for use with the first mandibular molars in the arch of FIG. 1.

Brackets 20, cemented to the lingual surfaces of the bicuspids of the mandibular arch of FIG. 1, are also included in the system, and these are shown in more detail in FIG. 4. Brackets 30 which are cemented to the lingual surfaces of the first molars are also included in the system of FIG. 1, and these are shown in more detail in FIG. 5. Bracket 30 is designed to fit into the anatomy of the lingual surfaces of the first mandibular molars for better adhesion. The external corners and edges of the bracket are smooth and rounded to prevent traumatizing the tongue. The bracket has a base 30b which is adhesively attached to the lingual surfaces of the mandibular first molars.

Figure 3:
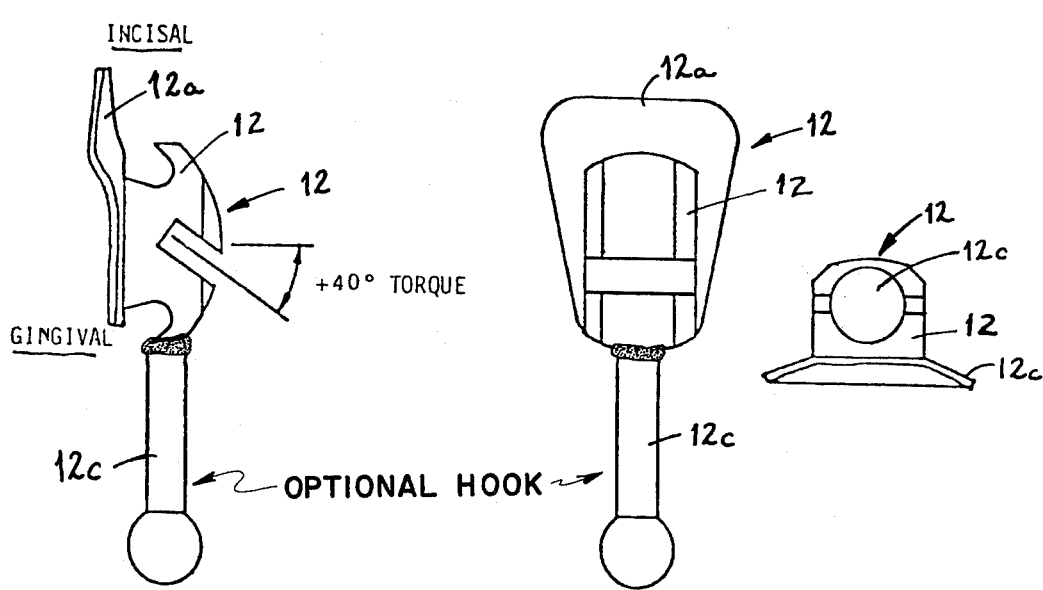
FIG. 3 represents three views of a lingual bracket suitable for use with the cuspids, or canines, of the arch of FIG. 1.

As shown in FIGS. 2 and 3, the configuration of the brackets 10, 11 and 12 for the mandibular central incisors, lateral incisors, and cuspids, is essentially the same. The only difference is the size of the bracket used in conjunction with the different teeth. As illustrated in FIGS. 2 and 3, the external edges of the brackets are rounded to avoid trauma to the tongue. There are no sharp corners, and the bracket profile is kept intentionally low to avoid crowding of the tongue space.

The bases of the brackets 10, 11 and 12 for the central incisors, lateral incisors and cuspids, as shown in FIGS. 2 and 3, are convex gingivally and straight incisally. The base is convex mesial/distally to fit into the marginal ridges of the teeth. The gingival portion of each bracket is tapered to conform with the gingival taper of the tooth while wider at the incisal portion as is the incisal portion of the tooth. The brackets are designed to fit between the lingual ridges of the teeth in intimate contact with the lingual tooth surface. This shaping of the brackets allows for optimal bonding of the brackets to the teeth, and for the uniform fit of the brackets onto the lingual surfaces of the teeth.

As shown in FIG. 2, bracket 10 includes a base portion 10a which is adhesively attached to the lingual surface of the tooth. The bracket also includes a portion 10b which is integral with the base 10a, but of somewhat smaller transverse dimensions than the base. A peripheral groove 18 extends between the portion 10b and base 10a for receiving an elastic, or metal, ligature 14, or other appropriate retaining means, for staying the arch wire 16 within a transverse slot 19 which extends across the portion 10b. The brackets 11 and 12, as shown in FIGS. 2 and 3, are similarly configured.

Figure 7:
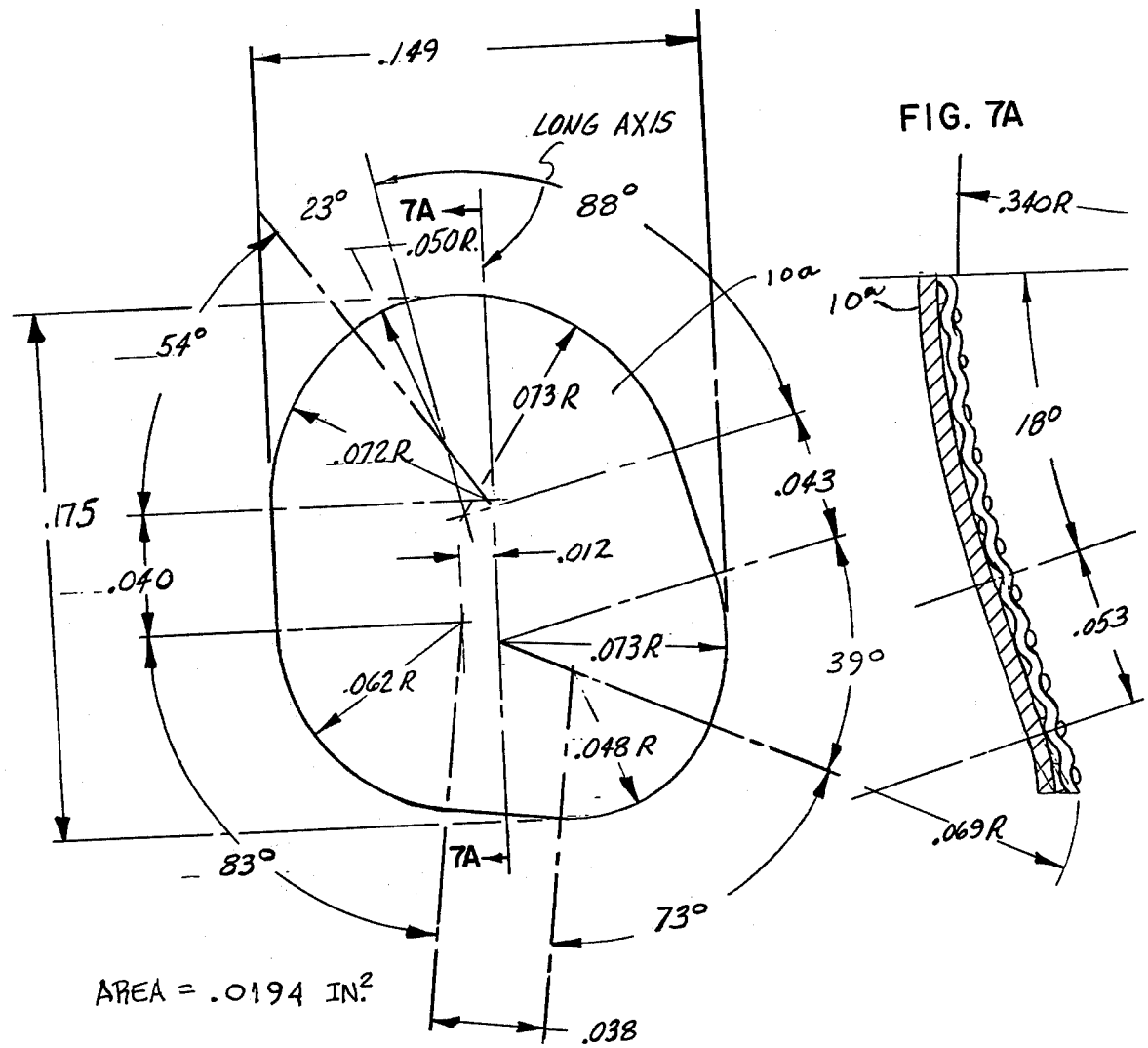
FIG. 7 is a represention of the face of a bracket to be mounted on the lingual surface of the central incisors of a patient.
Figure 8:
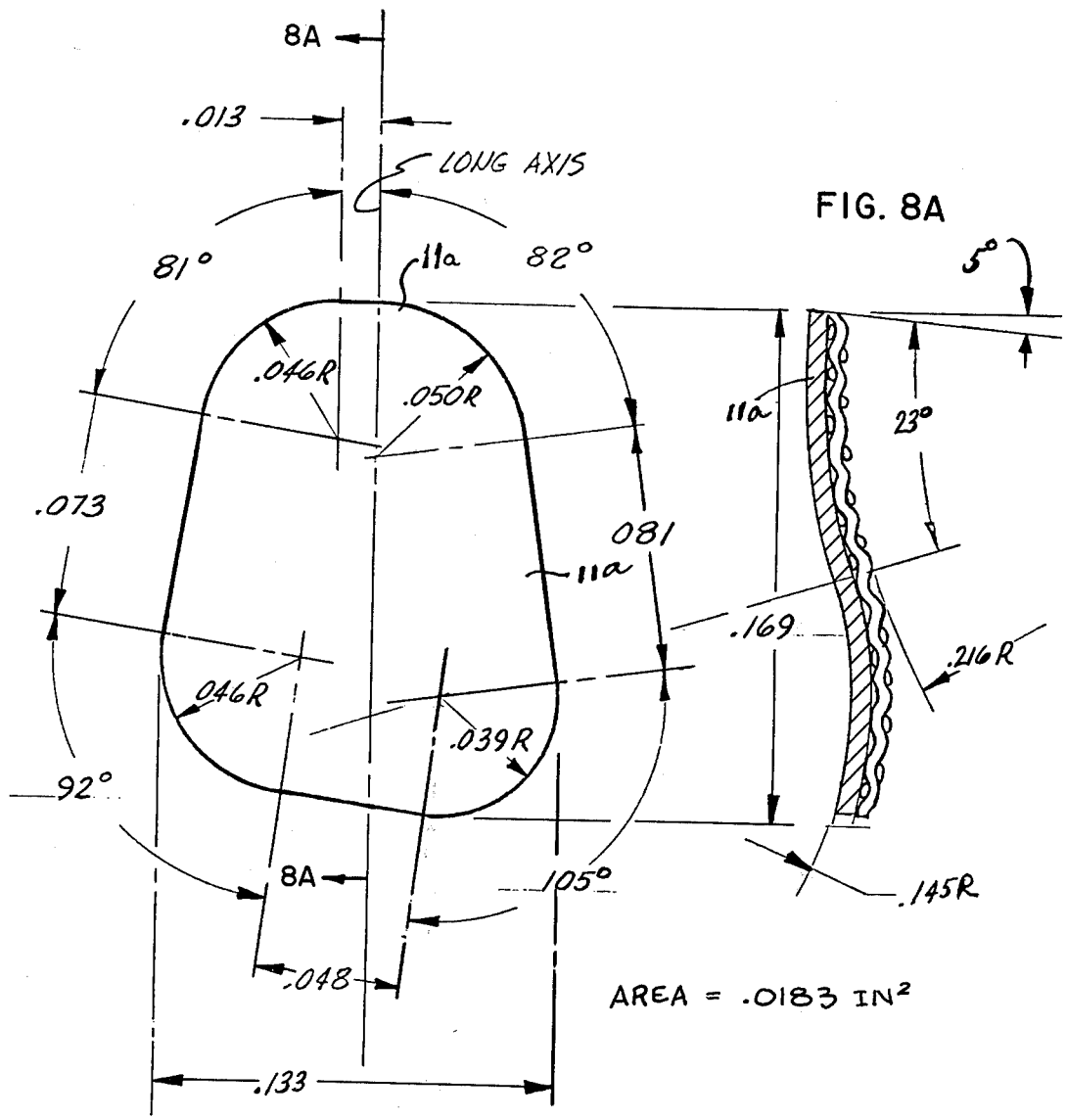
FIG. 8 is a representation of the face of the base of a bracket to be mounted on the lateral incisors of the patient.
Figure 9:
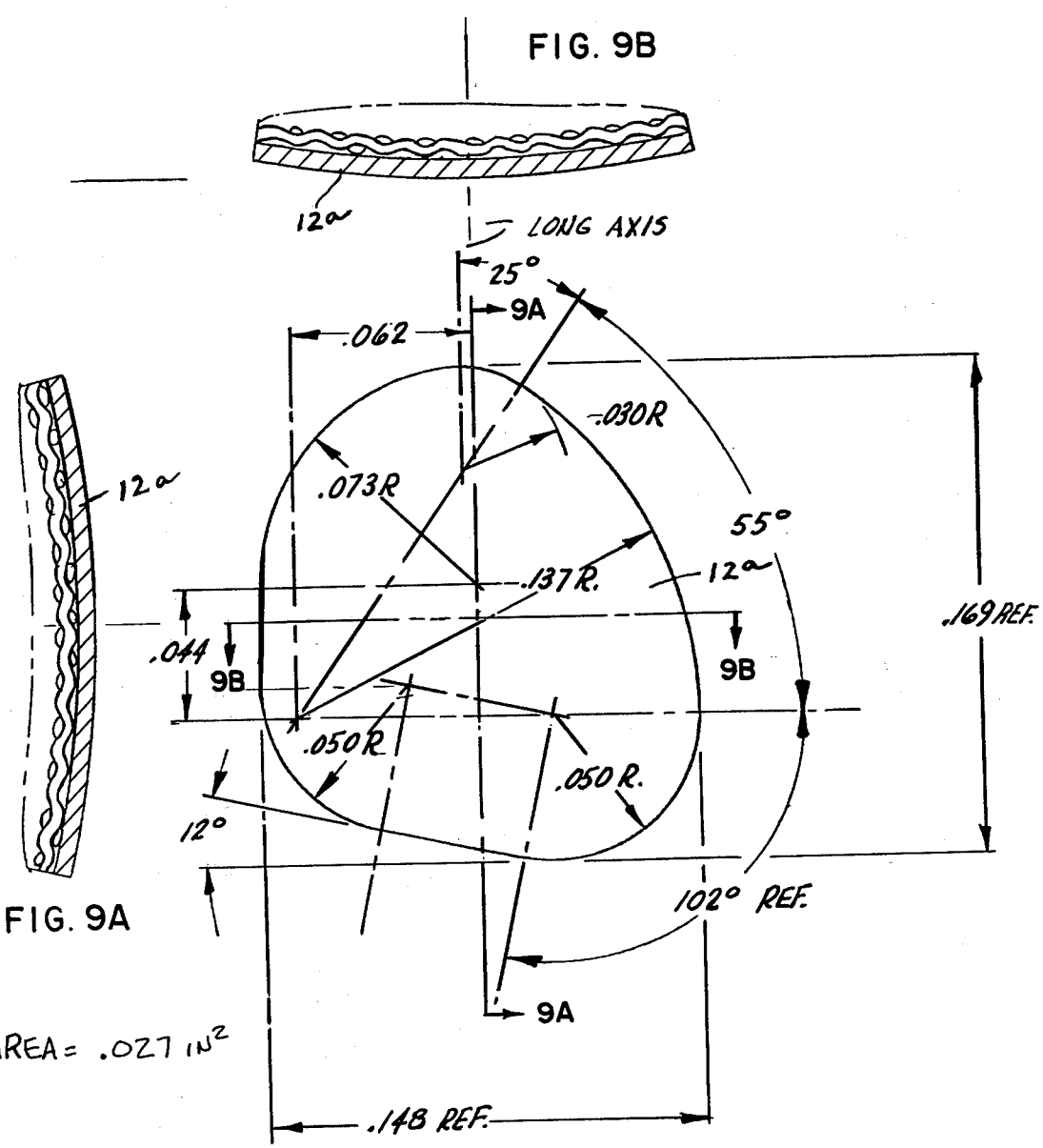
FIG. 9 is a representation of the face of the base of an attachment suitable for mounting on the cuspids (canines) of a patient.

The shaping of the brackets 10, 11 and 12 are such that a uniform fit onto the lingual surface of the teeth is assured, and for that purpose, the inner surface of the base 10a of bracket 10, of the base 11a of bracket 11, and of the base 12a of bracket 12, is as shown in the representations of FIGS. 7, 8 and 9. A specific torque and angulation for the respective bracket, for no in-and-out bends of the arch wire, is cut into the slope of slot 18, as indicated by the following tables:

Brackets 10 and 11

TORQUE: +46°
TIP: +2°
ROTATION: 0°
IN-OUT: 0
SLOT SIZE: 0.018

Also, as stated above, the base of each bracket has a thickness such that no in-and-out bends are required in the contoured arch wire 16.

As shown in FIG. 3, the bracket 12 is provided with an optional hook 12c. The slot in the attachment 12 has the illustrated angulation:

TORQUE: +40°
TIP: +9°
ROTATION: +4°
SLOT-SIZE: 0.018
IN-OUT: 0

The bracket 20 for the first and second mandibular bicuspids, as shown in FIG. 4, may include an optional hook 20a which, like the hook 12a of FIG. 3 may be a ball hook of a diameter of 0.028 inches which may be bent during the attachment of the bracket.

The transverse slot in bracket 20 is positioned to provide zero in-and-out for the arch wire by having the following parameters.

|  | First Bicuspid | Second Bicuspid |
| --- | --- | --- |
| TORQUE | +9° | +4° |
| TIP | −3° | −3° |
| ROTATION | −2° | −2° |
| SLOT SIZE | .018 | .018 |

As stated above, bracket 30 may be provided for the first mandibular molars, and it may include an optional hook 30a similar to the hooks described above. The transverse slot in the bracket has the following parameters for zero in-and-out bends of the arch wire.

TORQUE: −8°
TIP: −1°
ROTATION: 0°
SLOT SIZE: 0.018

Figure 6:
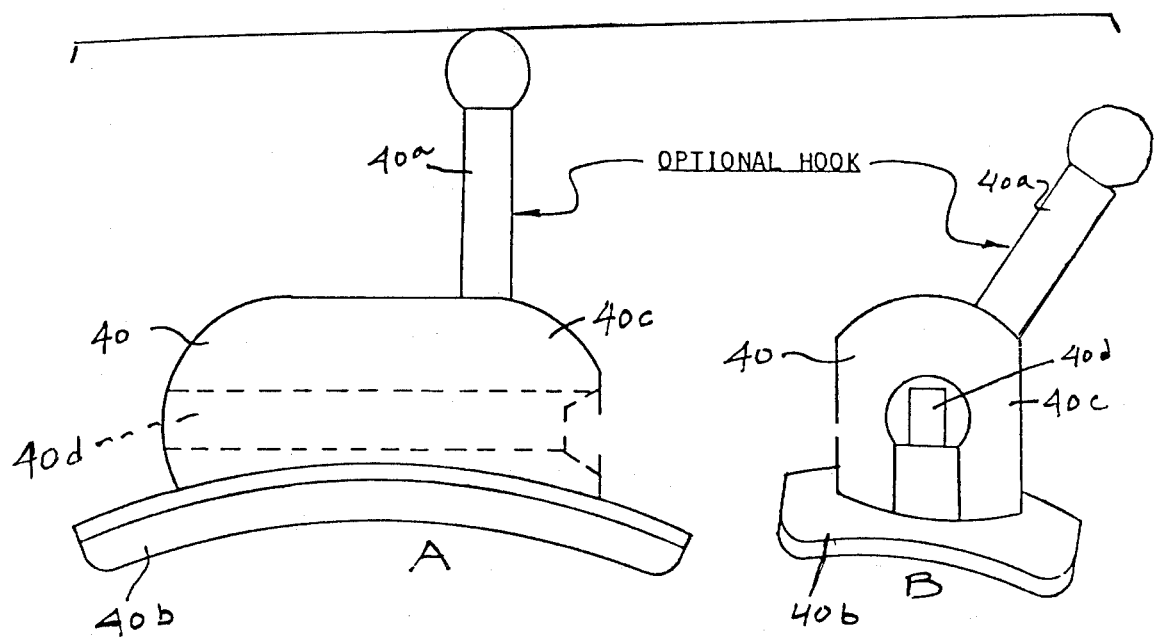
FIG. 6 is two views of a tube suitable for use in conjunction with either or both of the first or second molars in the arch of FIG. 1.

The tube 40, which can be used in conjunction with the second molar, and also with the first molar, is shown in detail in FIG. 6. The tube 40 of FIG. 6 includes a base 40b which is adhesively attached to the lingual surface of the mandibular molars. The tube also includes a portion 40c of reduced diameter with respect to the base, and integral therewith. The arch wire 16 extends through a central passage 40d in portion 40c. The central passage may be flared at one end, as shown, to facilitate the insertion of the arch wire. The passageway 40d is oriented as follows: −3° torque, −1° tip and −8° rotation when the tube is used in conjunction with the second molars; and −8° torque, −1° rotation when used in conjunction with the first molar.

Referring now to FIGS. 7, 8 and 9, and extensive topographical study was conducted on the teeth of hundreds of patients, and it was found that the tooth-engaging surfaces of the respective brackets used in conjunction with the central and lateral incisors and with the bicuspids could have a single standard shape and size and yet fit the vast majority of patients. These sizes and shapes are shown in FIGS. 7-9. In accordance with the invention, the base shown in FIG. 7 is especially dimensioned and shaped to fit the lingual surface of the central incisors of the majority of patients; the base shown in FIG. 8 is especially dimensioned and shaped to fit the lingual surfaces of the lateral incisors of the majority of patients; and the base shown in FIG. 9 is especially dimensioned and shaped to fit the lingual surfaces of the bicuspids of the majority of patients.

The following specifications for the brackets and tubes of the mandibular lingual appliance system of the invention are set forth below. It is to be understood that these specifications are listed merely by way of example, and are not meant to limit the invention in any way:

|  | Distal Base Length | Gingival/ Incisal Base Height | Gingival/ Occlusal Bracket Height | Mesio/ Distal Bracket Length | Mesio/ Distal Tip | Bucco/ Lingual Width |
| --- | --- | --- | --- | --- | --- | --- |
| Central | 3.5 m.m. | 5.5 m.m. | 5 | 3 | 2° | 2.5 m.m. |
| Lateral | 4 m.m. | 5.5 m.m. | 5 | 3.5 | 2° | 2.5 m.m. |
| Canine | 4.5 m.m. | 6 m.m. | 5.5 | 4 | 5° | 2.5 m.m. |
| 1st pre-molar | 3.5 m.m. | 4 m.m. | 3.5 | 4 | 2° | 2.5 m.m. |
| 2nd pre-molar | 4 m.m. | 4.5 m.m. | 4 | 4.5 | 2° | 2.5 m.m. |
| 1st molar | 7 m.m. | 3 m.m. | 2.5 | 5 m.m. | 2° | 2.5 m.m. |
| 2nd molar | 7 m.m. | 3 m.m. | 2.5 | 5 m.m. | 2° | 2.5 m.m. |

The lingual orthodontic system of the invention is a complete appliance from the second mandibular molar on one side of the arch to the second mandibular molar on the opposite side of the arch. The lingual appliance in one embodiment may be provided with no built-in labial/lingual or buccal/lingual torquing feature, and with no built-in mesio/distal tip or angulation feature.

In another embodiment, the lingual appliance of the invention may be provided that has all the built-in requirements of a straight wire appliance, specifically, standardized built-in base thickness so that no in or out bends are required of the arch wire, built-in labial/lingual and buccal/lingual torquing features, and built-in mesio/distal angulation capabilities.

The appliance of the invention may be all-metal, all-plastic, metal brackets and tubes with a laminated plastic base, part metal and part plastic brackets and tubes, with a plastic base.

The all-metal appliance has the advantage of being the strongest design and the metal arch wire moves with less friction in a metal slot reducing any drag and loss of efficiency during orthodontic movements. The metal brackets and tubes must have a perforated base or be provided with a screen attached to the base, so that they can be adhesively attached to the tooth surface.

The all-plastic appliance is not as strong as the all-metal appliance but provides a better bond to the tooth surface. To achieve maximal adhesion, it is desirable to combine the chemical bond of the adhesive with some mechanical retention, and this may be achieved by providing perforations in the plastic base.

The provision of metal brackets and tubes with plastic bases is desirable since chemical bonding of the adhesive and the base may be achieved for maximal adhesive strength, whereas the strength of the metal brackets and tubes is maximal. Also, as mentioned above, there is greater ease of the arch wire movement in the metal slot reducing friction drag of the arch wire during orthodontic movements. The metal brackets and tubes also provide accurate translation of the angulation and torque to the teeth.

Brackets and tubes that have part metal and part plastic, are the most aesthetic, may be adhesively attached to the teeth with a chemical bond for maximum strength, includes a metal part which translates the torque and tip accurately to the teeth, and gains strength from the metal so as to prevent breakage for occlusal trauma. The metal part of the slot increases the efficiency of the orthodontic movement for the metal arch wire since the wire slides better against the metal.

Accordingly, although a particular embodiment of the invention has been shown and described, modifications may be made. It is intended in the claims to cover the modifications which come within the spirit and scope of the invention.

What is claimed is:

1. A fixed lingual arch wire appliance system comprising: a first pair of brackets to be respectively adhesively attached to the lingual surfaces of the mandibular central incisors of a patient; a second pair of brackets to be respectively adhesively attached to the lingual surfaces of the mandibular lateral incisors of the patient; a third pair of brackets to be respectively adhesively attached to the lingual surfaces of the mandibular cuspids of the patient; each of said brackets having a base adhesively attached to a corresponding tooth, and said base being tapered to have a decreasing transverse dimension from the incisal end to the gigival end thereof, and said base being shaped to fit between the marginal lingual ridges of the corresponding tooth and to fit the anatomy of the lingual surface thereof, the tooth-engaging surface of the base of each of said first pair of brackets having dimensions and configuration shown schematically in FIG. 7, and FIG. 7A, the tooth-engaging surface of the base of each of said second pair of brackets having dimensions and configuration shown in FIG. 8, and FIG. 8A, and the tooth-engaging surface of the base of each of said third pair of brackets having dimensions and configuration shown schematically in FIG. 9, FIG. 9A, and FIG. 9B.

2. The appliance defined in claim 1, in which each of said brackets has a low profile, and rounded edges and corners, and is shaped to fit into and be confluent with the anatomy of the lingual surface of the corresponding tooth, so as to prevent trauma of the tongue.

3. The system defined in claim 1, in which each of the brackets has a transverse channel extending thereacross for receiving an arch wire, each of said channels having a particular buccal-lingual depth, torque angle, tip angle and rotation angle, to accept an arch wire without in-and-out bend requirements.

4. The system defined in claim 3, in which the transverse channel for each bracket of said first and second pairs has the following parameters: torque +46°, tip +2°, rotation 0°.

5. The system defined in claim 3, in which said transverse channel for each bracket of said third pair has the following parameters: torque 40°, tip +9°, rotation +4°.

6. A bracket for use in a fixed lingual arch wire appliance system to be adhesively attached to the lingual surface of a mandibular central incisor of a patient having a tooth-engaging surface with dimensions and configuration shown in FIG. 7, and FIG. 7A.

7. A bracket for use in a fixed lingual arch wire appliance system to be adhesively attached to the lingual surface of a mandibular lateral incisor of a patient having a tooth-engaging surface with dimensions and configuration shown in FIG. 8 and FIG. 8A.

8. A bracket for use in a fixed lingual arch wire appliance system to be adhesively attached to the lingual surface of a mandibular cuspid of a patient having a tooth-engaging surface with dimensions and configuration shown in FIG. 9, FIG. 9A, and FIG. 9B.

* * * * *